United States Patent
Tsuchida et al.

(10) Patent No.: US 8,343,556 B2
(45) Date of Patent: Jan. 1, 2013

(54) COMPOSITION FOR TREATING AND/OR PREVENTING PERIODONTAL DISEASE

(75) Inventors: Yuuzou Tsuchida, Shinagawa-ku (JP); Mitsuo Kawabe, Shinagawa-ku (JP); Kunitomo Watanabe, Gifu (JP); Kotarou Tsuchida, Shinagawa-ku (JP)

(73) Assignee: Hououdou Co., Ltd., Tokyo (JP)

( * ) Notice: Subject to any disclaimer, the term of this patent is extended or adjusted under 35 U.S.C. 154(b) by 0 days.

(21) Appl. No.: 11/838,158

(22) Filed: Aug. 13, 2007

(65) Prior Publication Data

US 2008/0014292 A1   Jan. 17, 2008

Related U.S. Application Data

(60) Division of application No. 11/340,796, filed on Jan. 27, 2006, now abandoned, which is a continuation of application No. PCT/JP2004/011210, filed on Jul. 29, 2004.

(30) Foreign Application Priority Data

Jul. 29, 2003  (JP) ................................. 2003-203199

(51) Int. Cl.
 *A61K 36/899* (2006.01)
 *A61K 8/02* (2006.01)
 *A61P 1/02* (2006.01)
 *A01N 25/34* (2006.01)

(52) U.S. Cl. ......... 424/750; 424/401; 424/404; 514/900

(58) Field of Classification Search .................. None
See application file for complete search history.

(56) References Cited

U.S. PATENT DOCUMENTS

| | | | |
|---|---|---|---|
| 3,124,506 A | * | 3/1964 | Holman et al. |
| 4,462,136 A | | 7/1984 | Nakao et al. |
| 4,886,657 A | | 12/1989 | Ratcliff |
| 5,100,652 A | | 3/1992 | Kross et al. |
| 6,187,324 B1 | | 2/2001 | Ogi et al. |
| 2005/0244515 A1 | | 11/2005 | Tsuchida et al. |
| 2006/0029627 A1 | | 2/2006 | Tsuchida et al. |
| 2006/0029689 A1 | | 2/2006 | Tsuchida et al. |
| 2006/0251752 A1 | | 11/2006 | Tsuchida et al. |

FOREIGN PATENT DOCUMENTS

| | | |
|---|---|---|
| CN | 1674925 A | 9/2005 |
| EP | 1304115 A1 | 4/2003 |
| EP | 1 491 203 A1 | 12/2004 |
| EP | 1 512 408 A1 | 3/2005 |
| JP | 54046815 A * | 4/1979 |
| JP | 57-85319 A | 5/1982 |
| JP | 01226806 A | 9/1989 |
| JP | 8-175946 A | 7/1996 |
| JP | 09094081 A * | 4/1997 |
| JP | 2001-151655 A | 6/2001 |
| WO | 00/67707 A1 | 11/2000 |
| WO | WO 03/080096 A1 | 10/2003 |
| WO | WO 03/105878 A1 | 12/2003 |

OTHER PUBLICATIONS

Van Chuyen, et al., "Antimicrobial Activity of Kumaza (*Sasa albo-marginata*)," *Agric. Biol, Chem.* 46(4):971-978 (1982).

Zhang et al., "Potentials of Bamboo in Traditional Chinese Medicine and Development of Health Products", World Science and Technology—Modernization of Traditional Chinese Medicine, vol. 2, No. 3 pp. 54-56 (2006).

* cited by examiner

*Primary Examiner* — Michele Flood
(74) *Attorney, Agent, or Firm* — Sughrue Mion, PLLC

(57) ABSTRACT

A method for treating periodontal disease, which comprises administering an effective amount of a composition to one in need of treatment of periodontal disease, the composition comprising a Sasa extract and an organic acid.

7 Claims, 2 Drawing Sheets

0 %

0.2 %

0 %

0.2 %

COMPOSITION FOR TREATING AND/OR PREVENTING PERIODONTAL DISEASE

CROSS REFERENCE TO RELATED APPLICATION

This application is a divisional of U.S. application Ser. No. 11/340,796 filed Jan. 27, 2006, which is a continuation of International Application No. PCT/JP2004/011210 filed Jul. 29, 2004, the disclosures of both of which are hereby incorporated by reference.

TECHNICAL FIELD

The present invention relates to a composition for treating and/or preventing the periodontal disease, which comprises an extract originated from the plant: Sasa (bamboo grass).

BACKGROUND ART

It has long been known that *Streptococcus mutans* is closely involved in the decayed teeth or caries.

Moreover, the periodontosis is related to the abnormal proliferation of periodontal disease-related microorganisms within periodontal pockets. In this connection, known examples of such periodontal disease-related microorganisms include *Actinobacillus actinomycetemcomitans, Porphyromonas gingivalis, Bacteroides forthythus, Prevotella intermedia, Fusobacterium nucleatum, Capnocytophaga* spp., corroding organisms (*Wolinella* spp., *Campylobacter gracilis*, and *Eikenella corrodens*), *Eubacterium* spp., and *Treponema* spp. and it has been known that these microorganisms each take part in the periodontal disease to a variety of degrees. Among these, the initial two kinds of or the first and second microorganisms (*Actinobacillus actinomycetemcomitans* and *Porphyromonas gingivalis*) have been regarded as important in the disease.

In addition, *Candida albicans* has been known as a causal bacterium for the "thrush (*candidal stomatitis*)" and there have recently been proposed some opinions which point out the close correlation between the abnormal proliferation of *Candida* spp. within the oral cavity and the periodontosis.

Incidentally, it has long been known that the extract from *Sasa albo-marginata* has an antimicrobial activity. For instance, there have been reported such antimicrobial activities as those against *Staphylococcus aureus, Pseudomonas aeruginosa* and *Escherichia coli*, which are known as causal bacteria for infectious diseases of wound and those against *Helicobacter pylori* known as a causal bacteria for the gastric ulcer. The inventors of this invention have already found that if such a Sasa extract is used in a concentration (as expressed in terms of the solid content) ranging from 1 to 10% by mass, preferably 2 to 8% by mass and more preferably 3 to 7% by mass, various effects can be obtained, which have never been achieved by the conventional extract having a low concentration. For instance, it has an improving effect for, for instance, atopy; it shows significant antipruritic effect; and it has likewise considerably improved wound-healing effect (see, for instance, WO 02/07745).

However, it has not yet been known whether or not the Sasa extract has the antimicrobial activity effective for any kind of bacteria and it has not likewise generally been known that an extract derived from a natural source, which shows an antimicrobial activity against bacteria, also shows an antimicrobial activity against fungi such as *Candida* spp.

DISCLOSURE OF THE INVENTION

Accordingly, it is an object of the present invention to provide a composition effective for the prevention and/or treatment of the periodontal disease.

The present invention provides a composition for treating and/or preventing the periodontal disease, which comprises an extract originated from the plant: Sasa (bamboo grass) (hereafter referred to as "Sasa extract").

The present invention also provides a composition for treating and/or preventing the periodontal disease, which comprises the Sasa extract and an organic acid.

The composition for treating and/or preventing the periodontal disease according to the present invention is preferably in the form of a cream.

In this specification, the term "periodontal disease" used is defined so as to include not only the "periodontosis" which has been said to be related to the abnormal proliferation of periodontal disease-related microorganisms, but also the "decayed teeth" in which Streptococcus mutans is closely involved. Accordingly, the composition for the prevention and/or treatment of the periodontal disease according to the present invention likewise includes a composition for treating and/or preventing the "periodontosis" as well as the "decayed teeth".

BEST MODE FOR CARRYING OUT THE INVENTION

Figure 1:
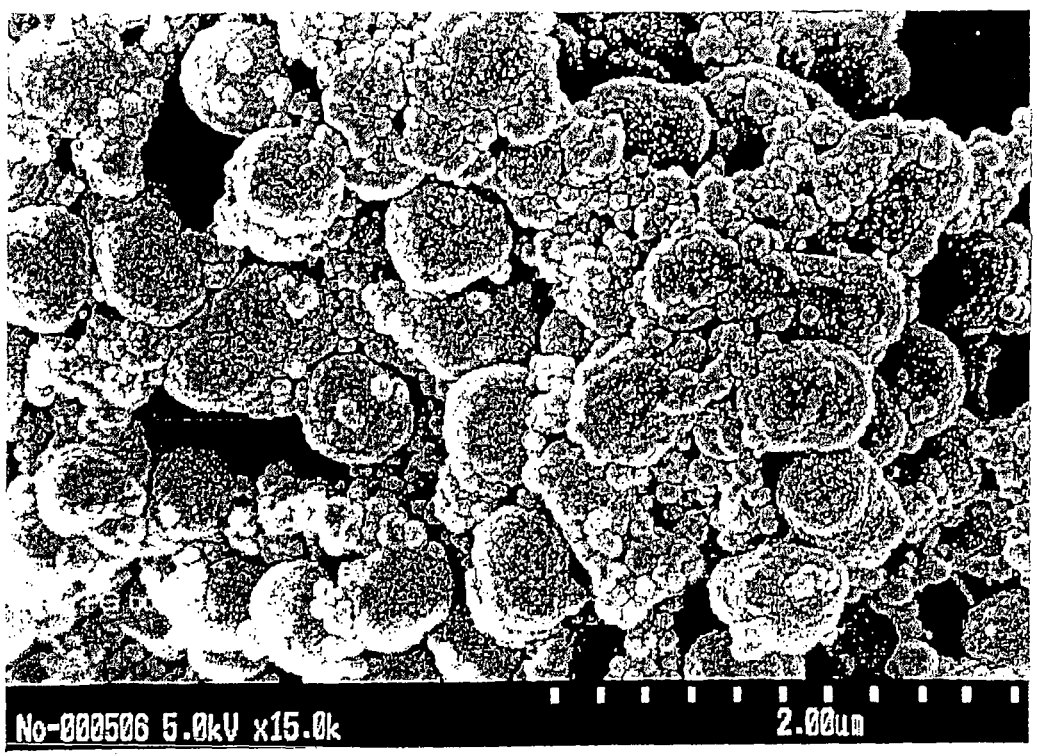
FIG. 1 is a scanning electron micrograph (SEM) (15,000×) of bacterial plaques grown on a culture medium not containing Sasa extract (TWEBS).

The inventors of this invention have variously investigated the antimicrobial activities of the Sasa extract against a variety of bacteria, have found that if the Sasa extract is used in a concentration (as expressed in terms of the solid content) ranging from 1 to 50% by mass, preferably 2 to 25% by mass and more preferably 4 to 15% by mass, it can show conspicuous antimicrobial activities against periodontal disease-related microorganisms (such as *Actinobacillus actinomycetem-comitans, Porphyromonas gingivalis, Bacteroides forthythus, Prevotella intermedia, Fusobacterium nucleatum, Capnocytophaga* spp., corroding organisms (*Wolinella* spp., *Campylobacter gracilis*, and *Eikenella corrodens*), *Eubacterium* spp. and *Treponema* spp.); decayed teeth-related microorganisms such as those belonging to *Streptococcus*; and fungi such as those belonging to *Candida* and that the antimicrobial activity of the Sasa extract can be improved by the incorporation of an organic acid such as malic acid into the same and have thus completed the present invention. In this respect, if the solid content of the Sasa extract is less than 1% by mass, the resulting product would show only a limited effect of treating and/or preventing the periodontal disease, while the use thereof in a concentration of higher than 50% by mass is not preferred because of its extremely high stimulation.

Sasa (bamboo grass) used as a raw material for the Sasa extract which is the effective component of the composition for treating and/or preventing the periodontal disease according to the present invention is not restricted to any specific one and all of the plants belonging to *Sasa Makino et Shibata*. Examples thereof include *Sasa paniculata Makino et Shibata, Sasa albo-marginata, Sasa kurilensis Makino et Shibata*, OKUYAMA Sasa, EZOMIYAMA Sasa, Sasa palmate Nakai, YAHIKO Sasa, *Sasa megaphylla Makino et Uchida*, MIYAMA Sasa, SENDAI Sasa, YUKAWA Sasa, ABOI Sasa and ONUKA Sasa. Among these Sasa plants, specific examples of commercially available ones include *Sasa paniculata Makino et Shibata* and *Sasa albo-marginata* (CHUGOKU Sasa and HIDA Sasa). For instance, preferred are water-extracts of *Sasa paniculata Makino et Shibata* and *Sasa albo-marginata* collected in, for instance, TESHIO Mountains in Hokkaido during the term extending from July to October.

The Sasa extract used in the present invention is preferably one prepared by extracting raw leaves or dried leaves of a Sasa plant, preferably dried leaves thereof with water maintained at a temperature ranging from 100 to 180° C. at ordinary pressure or while applying a pressure.

The extraction method is not restricted to any particular one, but usable herein includes, for instance, that disclosed in Japanese Patent No. 3,212,278 (Japanese Un-Examined Patent Publication Hei 11-196818). More specifically, leaves of a Sasa plant are extracted at a temperature ranging from 100 to 180° C. for 5 to 30 minutes using a pressurized hot water extraction device, the resulting extract is separated from a moisture-containing solid content (moisture content: 40 to 70%) in a moisture separator, thereafter the moisture-containing solid content is treated at a temperature ranging from 100 to 200° C. for 5 to 60 minutes in a saturated vapor-heating device, the solid content thus treated is again treated at 100 to 180° C. for 5 to 30 minutes using a pressurized hot water extraction device to give an extract and the extracts obtained in the first and second extraction steps are combined prior to practical use. Alternatively, it is also possible to use an extract obtained by extracting dried leaves of a Sasa plant with, for instance, water heated to 60 to 100° C. for 30 minutes to 12 hours.

Examples of commercially available Sasa extracts each comprising 50% by mass of the Sasa extract as expressed in terms of the solid content include "TWEBS" manufactured and sold by Hououdou Co., Ltd. and "AHSS" manufactured and sold by Chloroland Moshiri Co., Ltd.

The. Sasa extract thus obtained contains sulfur atom-containing components and the content thereof as expressed in terms of the amount of sulfur atom ranges from about 4 to 10 mg and usually about 6 to 9 mg per one gram of the solid content of the Sasa extract. Principal constituents of the sulfur atom-containing components are considered to be sulfur atom-containing amino acids.

The composition for treating and/or preventing periodontal disease according to the present invention comprises such sulfur atom-containing components derived from the Sasa extract in an amount preferably ranging from 4 to 500 mg, more preferably 8 to 250 mg and most preferably 16 to 150 mg per 100 g of the composition as expressed in terms of the amount of sulfur.

Moreover, the Sasa extract comprises tannin and the content thereof ranges from about 5 to 15% by mass on the basis of the solid content of the extract.

It is desirable that the composition for treating and/or preventing periodontal disease according to the present invention comprises tannin originated from the Sasa plant in an amount preferably ranging from 0.05 to 7.5% by mass and more preferably 0.1 to 6% by mass as expressed in terms of the solid content thereof.

The composition for treating and/or preventing periodontal disease according to the present invention may be one simply comprising the Sasa extract as an effective component, but the antimicrobial activity thereof can further be improved by the use of an appropriate amount of an organic acid in combination with the Sasa extract. Examples of such organic acids are malic acid, citric acid, lactic acid, oxalic acid, malonic acid, succinic acid, fumaric acid, acetic acid, benzoic acid, phenylacetic acid, salicylic acid and phenols. Particularly preferably used herein is malic acid.

The amount of the organic acid to be used preferably ranges from 0.01 to 5% by mass, more preferably 0.02 to 3% by mass and most preferably 0.05 to 1.5% by mass on the basis of the total mass of the composition for treating and/or preventing periodontal disease.

The composition for the treatment and/or prevention of the periodontal disease according to the present invention may comprise only the Sasa extract or the combination of the Sasa extract and an organic acid, or the resulting composition may further admixed with other components and/or a carrier. The dosage forms of the composition for the treatment and/or prevention of the periodontal disease may be liquid, solid or gaseous ones. The composition for the treatment and/or prevention of the periodontal disease may be administered through either the oral route or any parenteral route. Examples of the dosage forms of the composition are a tablet, a pill, a powdery preparation, a liquid preparation, a chewing gum, or various forms of foods such as a candy or starch jelly, a chocolate, bread, a cookie, buckwheat vermicelli and wheat vermicelli for the oral administration; and a tooth paste, a mouth wash, and dosage forms for the local administration (such as a cream and an ointment), for the parenteral administration. Examples of such dosage forms for the local administration are those obtained by impregnating a carrier such as gauze made of natural or synthetic fibers with the composition for the prevention and/or treatment of the periodontal disease according to the present invention.

Among these dosage forms, those for the local administration such as a cream and an ointment are preferably used since they are suitable for the direct application to an affected part suffering from the periodontal disease or a decayed tooth.

In the preparation of the composition for the treatment and/or prevention of the periodontal disease according to the present invention, which is in a variety of dosage forms, there may be used, for instance, a base component such as an oily component, a humectant and/or an antiseptic, which are commonly used in pharmaceutical compositions, cosmetic products, compositions applied to the skin and compositions intra-orally administered (such as a tooth paste and a mouth wash).

Water used in the composition for the prevention and/or treatment of the periodontal disease are not restricted to particular ones and examples thereof include tap water, natural water and purified water, but preferably used herein is highly purified water such as ion-exchange water.

Examples of oily components usable herein are oils derived from animals such as squalane, tallow, lard, horse fat, lanolin and beeswax; oils derived from vegetables such as olive oil, grape seed oil, palm oil, jojoba oil and germ oil (such as rice germ oil); and synthetic or semi-synthetic oils such as liquid paraffin, higher fatty acid esters (such as octyl palmitate, isopropyl palmitate and octyl dodecyl myristate) and silicone oil.

The oily components are used in appropriate combinations while taking into consideration the performance requirement, for instance, an ability of protecting the skin, an effect of imparting emollient (or an effect of preventing drying of the skin and imparting softness and resilience to the skin through the coverage of the skin surface with a thin film) and an ability of imparting refreshed feeling to the skin. In one of preferred examples of such combinations, the oily component comprises squalane, olive oil and octyl dodecyl myristate.

The composition for the treatment and/or prevention of the periodontal disease comprises a solid oil component such as stearic acid, stearyl alcohol, behenic acid, cetanol and VASELINE (petroleum jelly) to control the hardness and flowability of the resulting composition and the composition preferably comprises stearic acid and cetanol in combination.

When preparing the composition for the treatment and/or prevention of the periodontal disease according to the present invention in the form of a cream composition, a creaming agent is used to convert the mixture of the Sasa extract, water and an oily component into a cream. Such a creaming agent is not restricted to any particular one, but glycerin monostearate and a self-emulsifiable glycerin monostearate (a product obtained by incorporating an emulsifying agent into glycerin monostearate) are in general used in combination.

Moreover, the composition for the treatment and/or prevention of the periodontal disease according to the present invention may, if necessary, comprise other additives such as a stabilizer, a humectant (a wetting agent), a wound-healing agent, an antiseptic, a surfactant, a binder, a foaming agent, a sweetening agent, a refrigerant and/or an abrasive.

Examples of stabilizers are a combination of a carboxy vinyl polymer with potassium hydroxide; polyethylene glycol distearate; and magnesium phosphate. In particular, polyethylene glycol sesqui-stearate (a 1:1 mixture of polyethylene glycol distearate and polyethylene glycol monostearate) (the molecular weight of the polyethylene glycol ranging from 1000 to 20,000) is preferably used herein since it has high stability, is not separated into water and oil and the hardness required when the composition is applied to the skin in the form of a cream composition can effectively be controlled.

Examples of humectants (wetting agents) usable herein are sodium salt of hyaluronic acid, collagen, an aloe extract (in particular, the aloe extract (2) derived from Aloe arborescens is preferred), urea, 1,3-butylene glycol, glycerin, trehalose, sorbitol, amino acids and sodium salt of pyrrolidone carboxylic acid.

Examples of wound-healing agents usable herein are allantoin, di-potassium glycyrrhizinate, a glycyrrhiza extract and a mugwort extract.

The antiseptic is used subsidiarily since the Sasa extract has an antibiotic effect by nature. Examples of such antiseptics are sodium benzoate, lower alkyl esters of p-hydroxy benzoic acid (for instance, so-called paraben such as methyl, ethyl, propyl or butyl ester), sodium propionate, mixed fatty acid esters (a mixture of capric acid glyceryl, lauric acid glyceryl-2 and lauric acid polyglyceryl-10), phenoxy ethanol, light-sensitive substance No. 201 (yellow dye), and 1,2-pentanediol, with paraben, mixed fatty acid esters and 1,2-pentanediol being preferably used herein.

Examples of the foregoing surfactants are sodium N-acyl-L-glutamate and polyoxyethylene sorbitan monostearate.

Examples of the binders usable herein include sodium carboxymethyl cellulose; examples of the foaming agents are sodium lauryl sulfate, sodium lauroyl glutamate, and sodium lauroyl sarcosinate; examples of the sweetening agents are xylitol, sorbitol and saccharin sodium; examples of the refrigerants include mint essence; and examples of the abrasives are calcium phosphate, calcium hydrogen phosphate and silica.

In addition, the composition may, if required, comprise aroma components such as orange oil, lemon oil, bitter orange peel oil and perfumes.

Water and an organic acid as an optional component are added to the foregoing components to make the total amount of the resulting composition 100% by mass.

The following Table 1 shows preferred amounts (% by mass) of the foregoing ingredients required for preparing the composition for the treatment and/or prevention of the periodontal disease in the form of a cream composition. The amount of each component other than water is based on the total mass of the foregoing components other than water.

TABLE 1

| Component | Preferred range | More preferred range | Most preferred range |
|---|---|---|---|
| Sasa extract | 1 to 50 | 2 to 25 | 4 to 15 |
| Liquid oily component | 6 to 30 | 2 to 20 | 5 to 15 |
| Solid oily component | 2 to 35 | 3 to 25 | 5 to 15 |
| Creaming agent | 1 to 6 | 1.5 to 4 | 1.6 to 3 |
| Stabilizer | 0 to 2 | 0 to 1.5 | 0 to 1 |
| Humectant | 0 to 10 | 0.05 to 5 | 0.1 to 5 |
| Wound-healing agent | 0 to 2 | 0.05 to 1 | 0.1 to 0.5 |
| Aroma component | 0 to 5 | 0 to 3 | 0 to 1 |
| Organic acid | 0.01 to 5 | 0.1 to 3 | 0.5 to 1.5 |
| Water | Balance | Balance | Balance |

The foregoing components are introduced into a heating-mixing kettle equipped with a stirring blade and preferably an emulsifying apparatus and they are then admixed together at a temperature ranging from 70 to 90° C. for 1 to 2 hours to thus form a composition for treating and/or preventing the periodontal disease according to the present invention.

The composition for the treatment and/or prevention of the periodontal disease according to the present invention may be used in a variety of dosage forms such as an ointment, a liquid preparation, a jelly preparation, a gel-like preparation, an aerosol and other shapes, in addition to a cream composition, with a cream-like composition being preferably used herein because it can easily be used and show a considerably excellent effect. Moreover, the composition of the present invention may likewise be formed into a semi-solid or liquid product.

It is desirable to apply the composition for the treatment and/or prevention of the periodontal disease according to the present invention to the affected part such as the affected part of periodontal disease, the tooth root of a decayed tooth or the periodontium, in an appropriate amount on the order of, for instance, 0.1 to 1 g, at a frequency ranging from 1 to 5 times, usually 1 to 3 times a day, when it is used in the form of a cream composition. The amount and frequency of application of the composition may appropriately be changed while taking into consideration, for instance, the symptoms of the disease.

The composition for the treatment and/or prevention of the periodontal disease according to the present invention is desirably taken in an appropriate amount on the order of, for instance, 0.01 to 0.1 g/l kg of body weight at a frequency ranging from 1 to 5 times, usually 1 to 3 times a day, when it is administered through the parenteral route. The amount and frequency of application of the composition may appropriately be changed while taking into consideration, for instance, the symptoms of the disease.

The Sasa extract used in the composition for the treatment and/or prevention of the periodontal disease according to the present invention as the effective component is an extract originated from a plant belonging to the genus *Sasa Makino et Shibata* and a 1.25% by mass aqueous solution thereof does not show any toxicity to the 293 cells derived from human fetal kidney.

The composition for the treatment and/or prevention of the periodontal disease according to the present invention comprises the Sasa extract in an amount ranging from 1 to 50% by mass as expressed in terms of the solid content thereof and the composition thus shows significant antimicrobial activities against microorganisms such as periodontal disease-related microorganisms and bacteria belonging to *Candida*.

The following are preferred embodiments of the composition for the treatment and/or prevention of the periodontal disease according to the present invention:

1. A composition for the treatment and/or prevention of the periodontal disease comprises the Sasa extract (1 to 50% by mass as expressed in terms of the solid content), water, an oily component and a creaming agent.
2. The composition for the treatment and/or prevention of the periodontal disease as set forth in the foregoing item 1 in which the oily component is at least one member selected from the group consisting of animal oils, vegetable oils, synthetic oils and semi-synthetic oils.
3. The composition for the treatment and/or prevention of the periodontal disease as set forth in the foregoing item 1 in which the oily component is at least one member selected from the group consisting of squalane, tallow, lard, horse fat, lanolin, beeswax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic acid, cetanol and VASELINE (petroleum jelly).
4. The composition for the treatment and/or prevention of the periodontal disease as set forth in any one of the foregoing items 1 to 3 in which the creaming agent is a combination of glycerin monostearate with self-emulsifiable glycerin monostearate.
5. The composition for the treatment and/or prevention of the periodontal disease as set forth in any one of the foregoing items 1 to 4 in which it further comprises at least one component selected from the group consisting of an organic acid, a stabilizer, a humectant, a wound-healing agent, an antiseptic and a surfactant.
6. The composition for the treatment and/or prevention of the periodontal disease as set forth in the foregoing item 5 in which the stabilizer is at least one member selected from the group consisting of combinations of carboxy vinyl polymers with potassium hydroxide; and polyethylene glycol distearate.
7. The composition for the treatment and/or prevention of the periodontal disease as set forth in the foregoing item 5 in which the humectant is at least one member selected from the group consisting of sodium salt of hyaluronic acid, collagen, aloe extracts, urea, 1,3-butylene glycol, glycerin, trehalose, sorbitol, amino acids and sodium salt of pyrrolidone carboxylic acid.
8. The composition for the treatment and/or prevention of the periodontal disease as set forth in the foregoing item 5 in which the wound-healing agent is at least one member selected from the group consisting of allantoin, di-potassium glycyrrhizinate, glycyrrhiza extracts and mugwort extracts.
9. The composition for the treatment and/or prevention of the periodontal disease as set forth in the foregoing item 5 in which the antiseptic is at least one member selected from the group consisting of sodium benzoate, lower alkyl esters of p-hydroxy benzoic acid, sodium propionate, mixed fatty acid esters, phenoxy ethanol, 1,2-pentanediol and yellow dyes.
10. The composition for the treatment and/or prevention of the periodontal disease as set forth in the foregoing item 5 which further comprises at least one member selected from the group consisting of orange oil, lemon oil, bitter orange peel oil and perfumes.
11. A composition for the treatment and/or prevention of the periodontal disease which comprises the Sasa extract, water, an oily component, a creaming agent, a stabilizer, a humectant, a wound-healing-promoting agent, an antiseptic and a surfactant, wherein the oily component is at least one member selected from the group consisting of squalane, tallow, lard, horse fat, lanolin, beeswax, olive oil, grape seed oil, palm oil, jojoba oil, germ oil, liquid paraffin, octyl palmitate, isopropyl palmitate, octyl dodecyl myristate, silicone oil, stearic acid, stearyl alcohol, behenic acid, cetanol and VASELINE (petroleum jelly); the creaming agent is a combination of glycerin monostearate with self-emulsifiable glycerin monostearate; the stabilizer is at least one member selected from the group consisting of combinations of carboxy vinyl polymers with potassium hydroxide, and polyethylene glycol distearate; the humectant is at least one member selected from the group consisting of sodium salt of hyaluronic acid, collagen, aloe extracts, urea, 1,3-butylene glycol, glycerin, trehalose, sorbitol, amino acids and sodium salt of pyrrolidone carboxylic acid; the wound-healing agent is at least one member selected from the group consisting of allantoin, di-potassium glycyrrhizinate, glycyrrhiza extracts and mugwort extracts; the antiseptic is at least one member selected from the group consisting of sodium benzoate, lower alkyl esters of p-hydroxy benzoic acid, sodium propionate, mixed fatty acid esters, phenoxy ethanol, and yellow dyes; and the surfactant is sodium N-acyl-L-glutamate.
12. The composition for the treatment and/or prevention of the periodontal disease as set forth in the foregoing item 11 which further comprises at least one member selected from the group consisting of orange oil, lemon oil, bitter orange peel oil and perfumes.
13. The composition for the treatment and/or prevention of the periodontal disease as set forth in the foregoing item 1 which comprises the Sasa extract, water, squalane, olive oil, glycerin monostearate, self-emulsifiable glycerin monostearate, a carboxy vinyl polymer, potassium hydroxide, urea, 1,3-butylene glycol, allantoin, a lower alkyl ester of p-hydroxy benzoic acid, stearic acid, sodium N-acyl-L-glutamate and lemon oil.
14. The composition for the treatment and/or prevention of the periodontal disease as set forth in the foregoing item 1 which comprises the Sasa extract, water, squalane, olive oil, octyl dodecyl myristate, cetanol, glycerin monostearate, self-emulsifiable glycerin monostearate, a carboxy vinyl polymer, potassium hydroxide, urea, 1,3-butylene glycol, allantoin, a mixed fatty acid ester, stearic acid, sodium N-acyl-L-glutamate and orange oil.
15. The composition for the treatment and/or prevention of the periodontal disease as set forth in any one of the foregoing items 1 to 14 which comprises polyethylene glycol sesqui-stearate.
16. The composition for the treatment and/or prevention of the periodontal disease as set forth in any one of the foregoing items 1 to 15 in which the organic acid is at least one member selected from the group consisting of malic acid, citric acid, lactic acid, oxalic acid, malonic acid, succinic acid, fumaric acid, acetic acid, benzoic acid, phenylacetic acid, salicylic acid and phenols.

17. The composition for the treatment and/or prevention of the periodontal disease as set forth in the foregoing item 16 in which the organic acid is malic acid.

18. The composition for the treatment and/or prevention of the periodontal disease as set forth in the foregoing item 1 which comprises calcium hydrogen phosphate, water, sorbitol, glycerin, the Sasa extract, silica, cellulose gum, sodium lauryl sulfate, xylitol, mint essence, magnesium phosphate, sodium lauroyl sarcosine and sodium saccharine.

19. The composition for the treatment and/or prevention of the periodontal disease as set forth in the foregoing item 1 which comprises calcium hydrogen phosphate, water, sorbitol, glycerin, the Sasa extract, silica, cellulose gum, sodium lauroyl glutamate, xylitol, mint essence, magnesium phosphate and sodium lauroyl sarcosine.

20. The composition for the treatment and/or prevention of the periodontal disease as set forth in the foregoing item 1 which comprises water, sorbitol, glycerin, the Sasa extract, cellulose gum, sodium lauroyl glutamate, xylitol, mint essence, magnesium phosphate and sodium lauroyl sarcosine.

The present invention will be described in more detail with reference to the following Reference Examples, working Examples and Test Examples.

REFERENCE EXAMPLE 1

Preparation of Sasa Extract

Dried leaves of the Sasa plant collected in TESHIO Mountains in Hokkaido Japan in September were introduced into a pressurized hot water-extraction tank, treated at 125° C. for 10 minutes in the tank, the hot water was cooled down to about 80° C. by the action of a cooling water and then the resulting extract was separated from the moisture-containing solid contents using a screw-press in such a manner that the moisture content of the latter was controlled to a level of about 50% by mass. Then the solid contents having a moisture content of about 50% by mass were introduced into an autoclave and heat-treated under pressure at 180° C. for 10 minutes using saturated steam. The moisture-containing solid contents thus treated were again introduced into a pressurized hot water-extraction tank and treated at 110° C. for 5 minutes to thus obtain an extract. The extracts obtained in the first and second extraction steps were combined together, filtered through a diatomaceous earth layer, the resulting filtrate was concentrated under reduced pressure till the solid content thereof was increased to 50% by mass and the concentrate thus prepared was subjected to a fluidized sterilization treatment at a temperature ranging from 110 to 130° C. to give a Sasa extract.

The resulting Sasa extract was inspected for the sulfur content and it was found to be 3850 μm/ml (7.7 mg per one gram of the solid content).

REFERENCE EXAMPLE 2

The commercially available Sasa extract (Bambuseae Sasa) ("TWEBS" available from HOUOUDOU CO., LTD.) was inspected for the components present therein and the following results were obtained:

| Component | Amount (% by mass) |
|---|---|
| Water | 59.5 |
| Proteins | 8.6 |
| Lipids | 0.6 |
| Minerals | 9.0 |
| Carbohydrates | 19.8 |
| Tannin | 2.5 |

EXAMPLES 1 to 4

The components listed in the following Table 2 were admixed together in amounts (% by mass) likewise specified in Table 2, introduced into a heat-mixing kettle equipped with a stirring blade and an emulsifying apparatus and then mixed therein with stirring at 80° C. for 2 hours to thus give a composition for treating and/or preventing the periodontal disease according to the present invention. The added amounts of a Sasa extract having a solid content of 8% by mass (a product obtained by diluting, with water, the Sasa extract having a solid content of 50% by mass and prepared in Reference Example 1) were 12.5, 25, 37.5 and 75% by mass in Examples 1 to 4, respectively (therefore, the contents of the extract as expressed in terms of the solid contents thereof were 1, 2, 3 and 6% by mass; and sulfur contents of these samples were 7.7 mg, 15.4 mg, 23.1 mg and 46.2 mg per 100 g of the composition for treating and/or preventing the periodontal disease, respectively).

TABLE 2

| Component | Amount (% by mass) |
|---|---|
| Squalane | 5.0 |
| Olive oil | 6.0 |
| Lemon oil | 1.0 |
| Stearic acid | 4.0 |
| Glycerin monostearate | 0.8 |
| Carboxy vinyl polymer (CARBOPOL 940) | 0.2 |
| Glycerin monostearate (self-emulsifiable type) | 1.0 |
| Sodium N-acyl-L-glutamate | 0.2 |
| 1,3-Butylene glycol | 1.0 |
| Urea | 10.0 |
| Allantoin | 0.1 |
| Methyl p-oxy-benzoate | 0.1 |
| Propyl p-oxy-benzoate | 0.1 |
| Sasa extract (solid content: 8% by mass) | Desired amount |
| Potassium hydroxide | 0.02 |
| Ion-exchange water (Added to 100% by mass) | |

EXAMPLE 5

The same procedures used in Examples 1 to 4 were repeated using the components shown in the following Table 3 in the amounts likewise specified in Table 3 to thus give a composition for treating and/or preventing the periodontal disease according to the present invention.

TABLE 3

| Component | Amount (% by mass) |
|---|---|
| Squalane | 1.0 |
| Olive oil | 4.0 |
| Orange oil | 1.0 |
| Octyl dodecyl myristate | 6.0 |
| Stearic acid | 4.0 |
| Cetanol | 2.0 |

TABLE 3-continued

| Component | Amount (% by mass) |
|---|---|
| Polyethylene glycol distearate | 0.5 |
| Glycerin monostearate | 1.0 |
| Carboxy vinyl polymer (CARBOPOL 940) | 0.2 |
| Glycerin monostearate (self-emulsifiable type) | 1.4 |
| Sodium N-acyl-L-glutamate | 0.2 |
| 1,3-Butylene glycol | 1.0 |
| Urea | 3.0 |
| Allantoin | 0.1 |
| Mixed fatty acid ester (NIKOGUARD DL) | 0.5 |
| Sasa extract (solid content: 8% by mass) | 75.0 |
| Potassium hydroxide | 0.05 |
| Ion-exchange water (Added to 100% by mass) | |

The composition for treating and/or preventing the periodontal disease was found to have a sulfur content of 46.2 mg per 100 g of the composition.

EXAMPLE 6

The components listed in the following Table 4 were admixed together in amounts (% by mass) likewise specified in Table 4, introduced into a heat-mixing kettle equipped with a stirring blade and an emulsifying apparatus and then mixed therein with stirring at 80° C. for 2 hours to thus give a composition for treating and/or preventing the periodontal disease according to the present invention.

TABLE 4

| Component | Amount (% by mass) |
|---|---|
| Liquid paraffin | 10.0 |
| Squalane | 1.0 |
| Olive oil | 1.0 |
| Orange oil | 1.0 |
| Octyl dodecyl myristate | 6.0 |
| 1,2-Pentanediol | 0.5 |
| Phenoxy ethanol | 0.5 |
| Cetanol | 1.5 |
| Stearic acid | 4.0 |
| Glycerin monostearate | 2.0 |
| Glycerin monostearate (self-emulsifiable) | 2.5 |
| Polyethylene glycol distearate | 0.5 |
| Carboxy vinyl polymer | 0.3 |
| Sodium N-acyl-L-glutamate | 0.2 |
| 1,3-Butylene glycol | 1.0 |
| Ethanol | 3.0 |
| Trimethyl glycine | 0.5 |
| Sodium salt of hyaluronic acid | 1.0 |
| Sasa extract (solid content: 50% by mass) | 12.0 |
| Purified water | 51.5 |

The pH value of the resulting cream was found to be 6.00.

EXAMPLE 7

The components listed in the following Table 5 were admixed together in amounts (% by mass) likewise specified in Table 5, introduced into a heat-mixing kettle equipped with a stirring blade and an emulsifying apparatus and then mixed therein with stirring at 80° C. for 2 hours to thus give a cream or a composition for treating and/or preventing the periodontal disease according to the present invention.

TABLE 5

| Component | Amount (% by mass) |
|---|---|
| Olive oil | 3.0 |
| Squalane | 1.0 |
| Liquid paraffin | 3.0 |
| Cetanol | 1.3 |
| Glycerin monostearate | 2.0 |
| Glycerin monostearate (self-emulsifiable type) | 5.0 |
| Polyoxyethylene (20) stearyl ether | 1.0 |
| Polyoxyethylene (20) cetyl ether | 1.0 |
| Polyoxyethylene monostearate (140) | 1.0 |
| Bentonite | 0.5 |
| Xanthane gum | 0.2 |
| Glucono-δ-lactone | 4.0 |
| dl-Malic acid | 1.0 |
| Triethanolamine | 3.3 |
| 1,2-Pentanediol | 0.5 |
| Phenoxy ethanol | 0.5 |
| 1,3-Butylene glycol | 2.0 |
| Sasa extract (solid content: 50% by mass) | 12.0 |
| Purified water | 57.7 |

The pH value of the resulting cream was found to be 4.68.

EXAMPLE 8

The components listed in the following Table 6 were admixed together in amounts (% by mass) likewise specified in Table 6 to thus give a composition for treating and/or preventing the periodontal disease (tooth paste composition) according to the present invention.

TABLE 6

| Component | | Amt. (% by mass) |
|---|---|---|
| Calcium hydrogen phosphate | Abrasive | 30 to 40 |
| Sasa extract (solid content: 50% by mass) | | 25 |
| Sorbitol-containing liquid | Wetting agent | 10 to 30 |
| Glycerin | Wetting agent | 10 to 30 |
| Silica | Abrasive | 3 to 10 |
| Sodium carboxymethyl cellulose | Binder | 1 to 5 |
| Sodium lauryl sulfate | Foaming agent | 1 to 5 |
| dl-Malic acid | | 1 |
| Xylitol | Sweetening agent | Not more than 1 |
| Mint essence | Refrigerant | Not more than 1 |
| Magnesium phosphate | Stabilizer | Not more than 1 |
| Sodium lauroyl sarcosine | Foaming agent | Not more than 1 |
| Sodium saccharine | Sweetening agent | Not more than 1 |
| Purified water | | Balance |

EXAMPLES 9 to 11

The same procedures used in Example 7 except that the amounts of the Sasa extract (solid content: 50% by mass) were set at 16%, 20% and 30% by mass and that the amount of purified water was adjusted in proportion thereto to thus give cream compositions for treating and/or preventing the periodontal disease according to the present invention, each having a content of the Sasa extract (solid content) of 8%, 10% or 15% by mass, respectively.

EXAMPLE 12

The components listed in the following Table 7 were admixed together in amounts (% by mass) likewise specified in Table 7 to thus give a composition for treating and/or preventing the periodontal disease (tooth paste composition) according to the present invention.

TABLE 7

| Component | | Amt. (% by mass) |
|---|---|---|
| Calcium hydrogen phosphate | Abrasive | 30 to 40 |
| Sasa extract (solid content: 50% by mass) | | 25 |
| Sorbitol-containing liquid | Wetting agent | 10 to 30 |
| Glycerin | Wetting agent | 10 to 30 |
| Silica | Thickening agent | 3 to 10 |
| Sodium carboxymethyl cellulose | Binder | 1 to 5 |
| Sodium lauroyl glutamate | Foaming agent | 1 to 5 |
| dl-Malic acid | | 1 |
| Xylitol | Sweetening agent | Not more than 1 |
| Mint essence | Refrigerant | Not more than 1 |
| Magnesium phosphate | Stabilizer | Not more than 1 |
| Sodium lauroyl sarcosine | Foaming agent | Not more than 1 |
| Purified water | | Balance |

EXAMPLE 13

The components listed in the following Table 8 were admixed together in amounts (% by mass) likewise specified in Table 8 to thus give a composition for treating and/or preventing the periodontal disease (tooth paste composition) according to the present invention.

TABLE 8

| Component | | Amt. (% by mass) |
|---|---|---|
| Sasa extract (solid content: 50% by mass) | | 25 |
| Sorbitol-containing liquid | Wetting agent | 10 to 30 |
| Glycerin | Wetting agent | 10 to 30 |
| Silica | Thickening agent | 3 to 10 |
| Sodium carboxymethyl cellulose | Binder | 1 to 5 |
| Sodium lauroyl glutamate | Foaming agent | 1 to 5 |
| dl-Malic acid | | 1 |
| Xylitol | Sweetening agent | 3 to 10 |
| Mint essence | Refrigerant | Not more than 1 |
| Magnesium phosphate | Stabilizer | Not more than 1 |
| Sodium lauroyl sarcosine | Foaming agent | Not more than 1 |
| Purified water | | Balance |

TEST EXAMPLE 1

As a test solution, there was used "TWEBS" (a solution containing 50% by mass (as expressed in terms of the solid content) of the Sasa extract and 1% by mass of malic acid and having a pH value of about 5.0) available from HOUOUDOU CO., LTD. Sterilized distilled water was used as a diluent. Regarding bacteria, the test solution was in order diluted twofold to concentrations of 4, 2, 1 and 0.5%, while the concentration thereof was variously changed to 8, 7, 6, 5, 4, 3, 2 and 1% for the fungi belonging to Candida spp. to thus determine each corresponding minimum inhibitory concentration (MIC).

The minimum inhibitory concentration (MIC) was determined according to the agar plate-dilution technique using a GAM agar culture medium as the sensitivity-determining medium. The judgment was carried out after the cultivation under aerobic conditions over 24 hours for the facultative bacteria and after the cultivation under anaerobic conditions over 48 hours for the anaerobic bacteria. Each bacterium was inoculated at a bacterial density of about $10^6$ cells per spot. A 2N NaOH aqueous solution or a 10% hydrogen chloride aqueous solution was, if desired, used to control the pH value of the culture medium.

A fungus belonging to Candida spp. was cultivated on a Mycocell-agar culture medium (BD) over 48 hours to thus obtain a colony of each strain to be tested (test strain), the colony was dispersed in an MH broth (available from Difco) to obtain a bacterial cell dispersion having a turbidity of McFarland#1, and then one platinum loop (10 μl) each of the resulting bacterial cell dispersion was inoculated into a series of sample solution-containing plate culture mediums according to the streaking-smearing technique. In this respect, one platinum loop of the resulting bacterial cell dispersion included about $10^6$ bacterial cells. After cultivating each plate culture medium at 35° C. for 24 hours, the culture mediums were visually observed for the confirmation of whether the bacterial cells underwent proliferation or not. The case wherein the bacterial cells underwent proliferation was judged to be (+).

In addition, there were used Escherichia coli ATCC 25922 and Staphylococcus aureus ATCC 25923 as the strains for the management of the MIC precision.

There was used Streptococcus mutans GTC 218 as an example of the decayed tooth-related bacteria. On the other hand, there were used, as control bacteria, 5 strains of gram-positive cocci including Streptococcus pyogenes ATCC 19615 and Streptococcus pneumoniae ATCC 6305. These bacteria are pathogenic bacteria causing diseases of upper respiratory tracts such as the oral cavity and the pharyngeal cavity and it has been recognized that they do not belong to such decayed tooth-related bacteria. Pure-cultured bacteria aerobically cultivated on a blood-agar culture medium were used in the experiments.

Herein used as the periodontal disease-related microorganisms were Porphyromonas gingivalis ATCC 33277, Prevotella intermedia ATCC 25611, Bacteroides forthythus, Fusobacterium nucleatum ATCC 25586, Actinobacillus actinomycetemcomitans, and Capnocytophaga ohracea GAI-5586. These bacteria were subjected to the pure-cultivation on a Brucella HK blood-agar culture medium and the resulting pure-cultivated bacteria were used. In the cultivation, there were used anaerobic glove-boxes.

There were used 13 strains of Candida albicans and Candida glabrata in all. These strains were isolated from various kinds of clinical materials and stored in the anaerobic bacteria-experimental facilities affiliated with the medical department of Gifu University.

Results thus obtained are summarized in the following Tables 9 to 11.

TABLE 9

Antimicrobial Activities Against Decayed Tooth-Related Bacteria and Other Non-Related Cocci ($10^6 \cdot$ ml)

| Designation of Bacteria | MIC of Sasa Ext. Test Sample Soln. |
|---|---|
| Streptococcus mutans | 2.0 |
| Streptococcus pyogenes | 2.0 |
| Streptococcus pneumoniae | 0.5 |
| Streptococcus milleri group | 2.0 |
| Staphylococcus aureus | 4 |
| Enterococcus faecalis | >4 |

TABLE 10

Antimicrobial Activities Against Periodontal Disease-Related Bacteria ($10^7 \cdot$ ml)

| Designation of Bacteria | MIC of Sasa Ext. Test Sample Soln. (at pH 7) | MIC of Sasa Ext. Test Sample Soln. (at pH 6) |
|---|---|---|
| Porphyromonas gingivalis ATCC33277 | 0.5 | ND |
| Prevotella intermedia ATCC25611 | 1.0 | 2.0 |
| Bacteroides forthythus | NT | NT |

TABLE 10-continued

Antimicrobial Activities Against Periodontal
Disease-Related Bacteria ($10^7 \cdot$ ml)

| Designation of Bacteria | MIC of Sasa Ext. Test Sample Soln. (at pH 7) | MIC of Sasa Ext. Test Sample Soln. (at pH 6) |
|---|---|---|
| Fusobacterium nucleatum ATCC25586 | 2.0 | 2.0 |
| Actinobacillus actinomycetemcomitans | NT | NT |
| Capnocytophaga ohracea GAI-5586 | 2.0 | 0.5 |
| Campylobacter gracilis | NT | NT |

TABLE 11

Anti-fungal Activities Against *C. albicans*
and *C. glabrata* ($10^{6} \cdot$ ml)

| MIC of Sasa Ext. Test Sample Soln. (%) | Candida albicans strain | | Candida glabrata strain |
|---|---|---|---|
| | pH 5 | pH 7 | pH 5 |
| 8 | — | — | — |
| 7 | — | — | — |
| 6 | — | — | — |
| 5 | 1 | 3 | — |
| 4 | 4 | 5 | 4 |
| 3 | 3 | — | 1 |
| 2 | — | — | — |
| 1 | — | — | — |
| ND (Not Determinable) | — | — | — |
| Sum | 8 | 8 | 5 |

Conclusion:

The Sasa extract of the present invention inhibited the growth of *S. mutans* at a concentration of 2% under acidic conditions (at a pH value ranging from 6.0 to 5.0). The Sasa extract likewise inhibited the growth of the 4 kinds of periodontal disease-related bacteria examined above at a concentration of 2% under the same growth conditions. Moreover, the Sasa extract inhibited the growth of the fungi belonging to *Candida* spp. at a concentration of 5%.

TEST EXAMPLE 2

Ability of Sub-MIC Concentration of TWEBS to Reduce Amount of Extracellular Secretion of *Porphyromonas gingivalis* (Pg bacterium)

The term "dental plaque" herein used means the bio-film formed on a tooth. This bio-film is constituted by a colony or mass of a plurality of bacteria living in and buried in the polymers originated from the bacteria and/or those originated from the saliva (Eps: Extracellular polysaccharide substances or glycocalyx). The bio-film formed on the surface of a tooth is characterized in that it is quite hardly peeled off unlike those formed on the surface of the oral mucosa and that of the mucosa of tongue and further it would hardly be affected by a variety of antibacterial substances. Accordingly, it has been recognized that the dental plaque is quite important as a cause of the periodontal disease. It is important to destroy the same for the treatment of the periodontal disease and therefore, various studies have been conducted.

Incidentally, Pg bacterium is one of the most important anaerobic bacteria relating to the periodontal disease and it has been known that the bacterium can produce a powerful protease and that it plays an important role in the destruction of the gingiva. The Pg bacteria extracellularly produce glycocalyx. In addition, the protease produced by the Pg bacteria is extracellularly released by vesicles.

As previously shown in Test Example 1, it has been found that TWEBS has an extremely high antimicrobial activity against the Pg bacteria and that it can inhibit the growth of the bacteria at a concentration of 0.5%. In this Test Example, TWEBS was investigated for the effect thereof on the glycocalyx-producing ability of the Pg bacteria.

Methods for Experiments

Bacterial Strain Used: *Porphyromonas gingivalis* ATCC33277

The minimum inhibitory concentration (MIC) of TWEBS for this bacterial strain is not more than 0.5%.

Culture Medium: Modified GAM Agar Medium (available from Nissui Co., Ltd.)

Cultivation: Bacteria were cultivated according to the anaerobic cultivation technique using ANEROPACK (available from Sugiyamagen Co., Ltd).

Method: The Pg bacteria were grown on the modified GAM agar culture medium containing the sub-MIC concentration of TWEBS and the resulting bacterial plaques were observed under an electron microscope (SEM, TEM).

Results:

A. Visual Observation of Bacterial Plaques Grown on Modified GAM Culture Medium

1) There were collected the bacterial plaques grown on the culture medium in the presence of 0.2% TWEBS and those grown on the culture medium not containing TWEBS using a spreader. The bacterial plaques grown in the presence of 0.2% TWEBS was definitely less viscous as compared with those grown on the culture medium not containing TWEBS. There was likewise observed significant difference between them in the ability to diffuse in a fixing solution.

B. Observation of Bacterial Plaques Grown in the Presence of 0.2% TWEBS under Scanning Electron Microscope (SEM)

Figure 3:
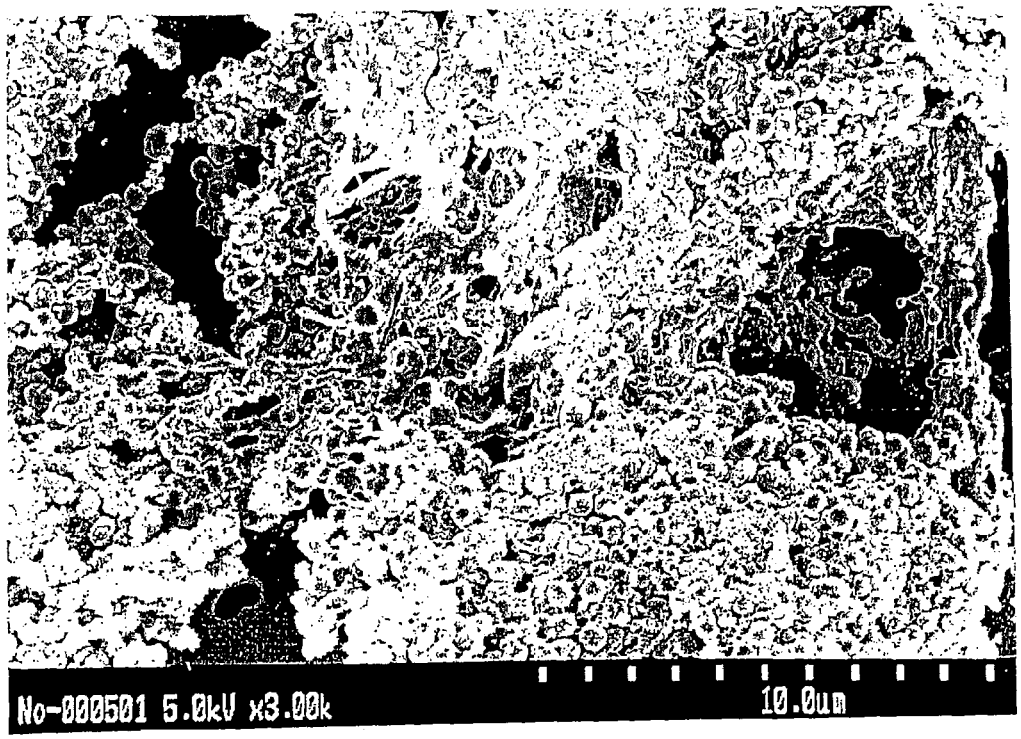
FIG. 3 is a scanning electron micrograph (SEM) (3,000×) of bacterial plaques grown on a culture medium not containing Sasa extract (TWEBS).

1) There were observed the presence of a large amount of a glycocalyx-like secretion in the peripheral region of the Pg bacteria grown on the culture medium not containing TWEBS and there were observed images, in which bacterial cell bodies were covered with glycocalyx, throughout the surface of the culture medium (FIGS. 1 and 3).

Figure 2:
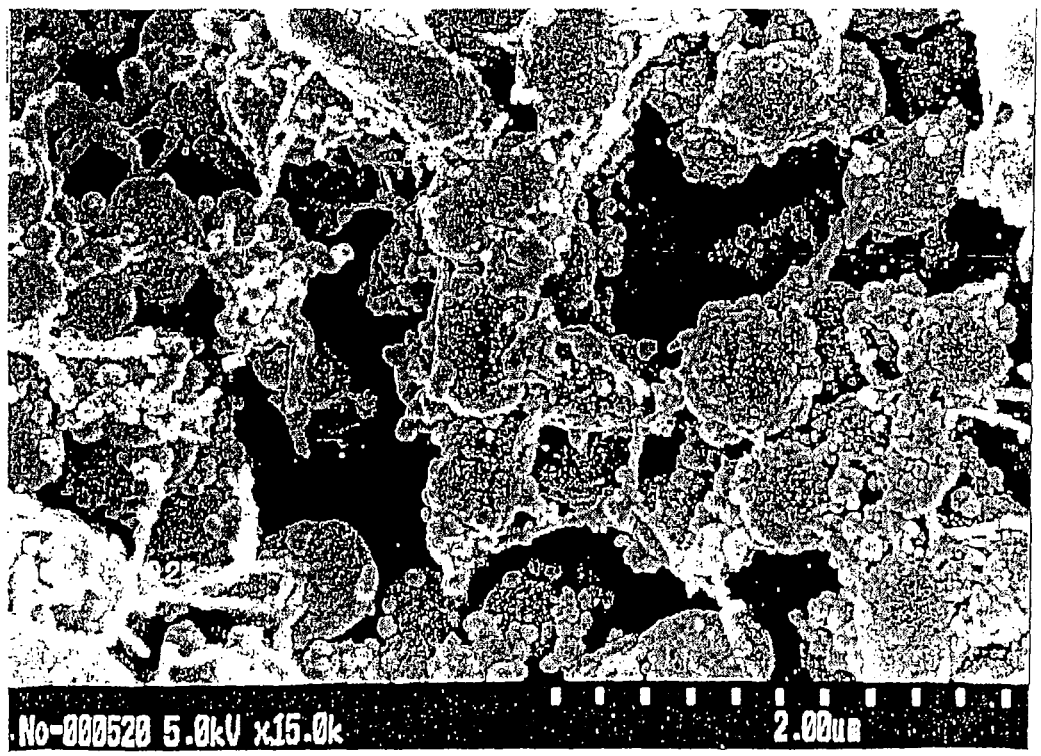
FIG. 2 is a scanning electron micrograph (SEM) (15,000×) of bacterial plaques grown on a culture medium in the presence of 0.2% of the Sasa extract (TWEBS).
Figure 4:
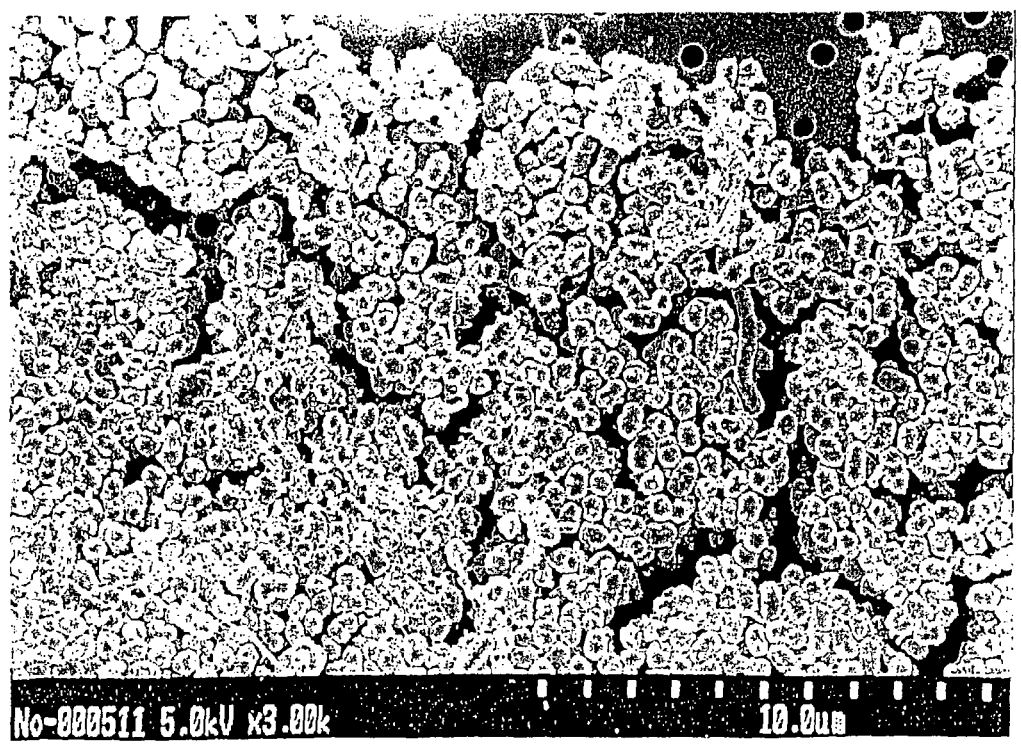
FIG. 4 is a scanning electron micrograph (SEM) (3,000×) of bacterial plaques grown on a culture medium in the presence of 0.2% of the Sasa extract (TWEBS).

2) On the other hand, there was observed only a small amount of such a glycocalyx-like secretion in the peripheral region of the Pg bacteria grown on the 0.2% TWEBS-containing culture medium and therefore, there were observed quite small number of images in which bacterial cell bodies were covered with glycocalyx. More specifically, there were observed images in which only a small amount of such a secretion was present in the peripheral region of the Pg bacteria and bacterial cell bodies were exposed (FIGS. 2 and 4).

There was observed the presence of vesicle-like structures in the peripheral region of the Pg bacterial cell bodies.

Conclusion:

It is clear from the results of Test Example 1 that TWEBS inhibits the proliferation of Pg bacteria at such a lower concentration on the order of not more than 0.5% (MIC: 0.5%), while the results obtained in Test Example 2 clearly indicate that TWEBS prevents the production or release of an extracellular substance originated from the Pg bacteria, which may be considered as glycocalyx, at the so-called sub-MIC concentration (0.2%) lower than the MIC.

Industrial Applicability

The composition of the present invention is useful as a composition for treating and/or preventing periodontal disease such as "periodontosis" which is assumed to be related to the abnormal proliferation of periodontal disease-related microorganisms within periodontal pockets and "decayed tooth" in which *Streptococcus mutans* is closely involved.

What is claimed is:

1. A method for treating periodontal disease comprising:
   administering an effective amount of a composition to a part in an oral cavity in which there is/are abnormal proliferation of a periodontal disease-related bacteria, a decayed teeth-related bacteria, and/or *Candida* spp.,
   (a) wherein said composition comprises a Sasa extract and malic acid,
   (b) wherein said Sasa extract is prepared by extracting raw leaves or dried leaves with water,
   (c) wherein said Sasa extract is contained in a concentration as expressed in terms of the solid content ranging from 2 to 25% by mass, and
   (d) wherein said malic acid is contained in a concentration of from 0.01 to 5% by mass.

2. The method according to claim 1, wherein the composition is administered in an amount of 0.01 to 0.1 g/1 kg of body weight, at a frequency of 1 to 5 times a day.

3. The method according to claim 1, wherein the composition is administered in an amount of 0.1 to 1 g, at a frequency of 1 to 5 times a day.

4. The method according to claim 1, wherein said malic acid is contained in a concentration of from 0.02 to 3% by mass.

5. The method according to claim 2, wherein said malic acid is in a concentration of from 0.02 to 3% by mass.

6. The method according to claim 1, wherein said composition further comprises an oily component and a creaming agent,
   said oily component is at least one member selected from the group consisting of squalane, tallow, lard, horse fat, lanolin, beeswax, olive oil, grape seed oil, palm oil, jojoba oil, germ oil, liquid paraffin, octyl palmitate, isopropyl palmitate, octyl dodecy myristate, silicone oil, stearic acid, stearyl alcohol, behenic acid, cetanol and petroleum jelly, and
   said creaming agent is a combination of glycerin monostearate with self-emulsifiable glycerin monostearate.

7. The method according to claim 1, wherein said composition is in the form of a cream.

* * * * *